US 8,852,162 B2

(12) United States Patent
Williams et al.

(10) Patent No.: US 8,852,162 B2
(45) Date of Patent: *Oct. 7, 2014

(54) DEVICE, METHOD, AND COMPUTER PROGRAM PRODUCT FOR DISPENSING MEDIA AS PART OF A MEDICAL PROCEDURE

(75) Inventors: Robert Williams, Fort Solonga, NY (US); Steven Hartman, Commack, NY (US); Philip Waldstein, Monroe, CT (US)

(73) Assignee: Acist Medical Systems, Inc., Eden Prairie, MN (US)

(*) Notice: Subject to any disclaimer, the term of this patent is extended or adjusted under 35 U.S.C. 154(b) by 1007 days.

This patent is subject to a terminal disclaimer.

(21) Appl. No.: 12/940,553

(22) Filed: Nov. 5, 2010

(65) Prior Publication Data

US 2011/0054311 A1 Mar. 3, 2011

Related U.S. Application Data

(63) Continuation of application No. 10/579,709, filed as application No. PCT/US2004/039620 on Nov. 24, 2004, now Pat. No. 7,850,640.

(60) Provisional application No. 60/525,315, filed on Nov. 26, 2003, provisional application No. 60/525,778, filed on Nov. 26, 2003.

(51) Int. Cl.
*A61M 31/00* (2006.01)
*A61M 5/172* (2006.01)
*A61M 5/168* (2006.01)
*A61M 5/00* (2006.01)

(52) U.S. Cl.
CPC ............ *A61M 5/172* (2013.01); *A61M 5/16827* (2013.01); *A61M 5/007* (2013.01)
USPC ........................................ 604/500

(58) Field of Classification Search
USPC ................. 604/65–67, 131, 890.1, 500–522; 128/DIG. 12, DIG. 13, DIG. 1
See application file for complete search history.

(56) References Cited

U.S. PATENT DOCUMENTS 3,631,847 A 1/1972 Hobbs
3,701,345 A 10/1972 Heilman et al.
(Continued)

FOREIGN PATENT DOCUMENTS

JP 10-70631 A 3/1998
KR 10-2004-0107634 A 12/2004
(Continued)

OTHER PUBLICATIONS

Supplemental European Search Report for Application No. EP 04 81 2191 dated Jul. 29, 2010.
(Continued)

*Primary Examiner* — Manuel Mendez
(74) *Attorney, Agent, or Firm* — Fredrikson & Byron, P.A.

(57) ABSTRACT

A device, method, and computer program product for controlling a dispensing device adapted to be capable of dispensing contrast media as part of a medical imaging procedure. The device comprises a controller device, user interface, injector portion, and a storage device such that a user of the device may initialize multiple dispensing functions in the injector portion and user interface via a user input. The method and computer program product for controlling a dispensing device comprises receiving a user input from a user interface and directing the dispensing device to perform multiple dispensing functions, including actuating the injector portion and updating the user interface, in response to a user input.

23 Claims, 4 Drawing Sheets

(56) References Cited

U.S. PATENT DOCUMENTS

| | | | |
|---|---|---|---|
| 4,006,736 | A | 2/1977 | Kranys et al. |
| 4,180,067 | A | 12/1979 | Derlien |
| 4,650,465 | A | 3/1987 | Langer et al. |
| 4,695,271 | A | 9/1987 | Goethel |
| 4,854,324 | A | 8/1989 | Hirschman et al. |
| 5,300,031 | A | 4/1994 | Neer et al. |
| 5,319,363 | A | 6/1994 | Welch et al. |
| 5,647,853 | A | 7/1997 | Feldmann et al. |
| 5,662,612 | A | 9/1997 | Niehoff |
| 5,681,286 | A | 10/1997 | Niehoff |
| 5,719,761 | A | 2/1998 | Gatti et al. |
| 5,868,710 | A | 2/1999 | Battiato et al. |
| 5,885,245 | A | 3/1999 | Lynch et al. |
| 5,928,197 | A | 7/1999 | Niehoff |
| 6,004,285 | A | 12/1999 | Sugahara |
| 6,171,276 | B1 | 1/2001 | Lippe et al. |
| 6,269,340 | B1 | 7/2001 | Ford et al. |
| 6,339,718 | B1 | 1/2002 | Zatezalo et al. |
| 6,929,619 | B2 | 8/2005 | Fago et al. |
| 7,264,148 | B2 | 9/2007 | Tachibana |
| 7,850,640 | B2 * | 12/2010 | Williams et al. ............ 604/65 |

FOREIGN PATENT DOCUMENTS

| | | |
|---|---|---|
| WO | WO 03/005891 A1 | 1/2003 |
| WO | WO 03/024385 A1 | 3/2003 |

OTHER PUBLICATIONS

Ezem, Inc; "There is only one choice in CT injector systems", pp. 1-8; Copyright 1995, E-Z-EM, Inc.

Ezem, Inc.; "PercuPump—Touch Screen CT Injector System"; Maintenance and Service Manual; Copyright 1996, E-Z-EM, Inc.; Item No. 1471152, Jun. 15, 1996; 81 Pages.

Ezem, Inc.; "PercuPump II—Touch Screen CT Injector System"; Manual and Operations Guide; Copyright 1995, E-Z-EM, Inc.; Item No. 1470891; 51 Pages.

Liebel-Flarsheim; Angiomat 6000 Contrast Delivery System Advertisement; 1992; Copyright 1992; 8 Pages.

Liebel-Flarsham; Angiomat 6000 Digital Injection System, Installation and Service Manual, 601910; Jan. 1992.

Liebel-Flarsheim; Angiomat 6000 Digital Injection System, Operator's Manual 601905; Jan. 1992.

Liebel-Flarsheim; Angiomat 6000 Digital Injection System, Parts Manual 600995; Dec. 1991.

Liebel-Flarsheim; Angiomat CT Digital Injection System 115 V, Installation & Service Manual for M3 Models 600980; Dec. 1988.

Liebel-Flarsheim; Angiomat CT Digital Injection System Operator's Manual, 600964; Jul. 1990.

Liebel-Flarsheim; Angiomat CT Digital Injection System 115 V, Parts Manual 600977.

Liebel-Flarsheim, CT 9000 Contrast Delivery System Advertisement ; 1992.

Liebel-Flarsheim, CT 9000 Digital Injection System Operator's Manual, 800950; 1995.

Liebel-Flarsheim, CT 9000 ADV Digital Injection System Operator's Manual, 800731-A, Nov. 1997.

Liebel-Flarsheim, CT 9000 ADV Digital Injection System Operator's Manual, 800731-B, Jul. 1998.

Liebel-Flarsheim, Angiographic & CT Injectors Advertisement, 1992.

* cited by examiner

SEQUENTIAL AUTO-INITIALIZE

SEQUENTIAL AUTO-FILL

SEQUENTIAL REPLACE SYRINGE

DEVICE, METHOD, AND COMPUTER PROGRAM PRODUCT FOR DISPENSING MEDIA AS PART OF A MEDICAL PROCEDURE

CROSS REFERENCE TO RELATED APPLICATIONS

The present application is a continuation of U.S. application Ser. No. 10/579,709 filed Mar. 29, 2007 now U.S. Pat. No. 7,850,640, which was the National Stage of International Application No. PCT/US04/39620 filed Nov. 24, 2004, which claims priority to U.S. Provisional Application No. 60/525,315 filed Nov. 26, 2003 and U.S. Provisional Application No. 60/525,778 filed Nov. 26, 2003, each of which is incorporated by reference in its entirety herein.

FIELD OF THE INVENTION

The present invention relates generally to the dispensing of media used during the course of a number of medical procedures. In alternative embodiments, the present invention relates to the configuration and control of a dispensing device such that clinical personnel may control and/or configure the dispensing device in a more efficient manner from, in some cases, a remote location such as a control room or other control location that is not co-located with the dispensing device or dispensing portions of the dispensing device. The present invention provides a system, method, and computer program product that may be integrated into a medical imaging suite and in communication with one or more injector systems, a computer network, and/or one or more extravasation detection devices so as to allow, for example, the pre-configuration of the dispensing device, the pre-loading of the dispensing device with one or more media (such as contrast media and/or flushing media), the post-dispensing configuration of the dispensing device, and other control and configuration functions related to the use of the dispensing device. The embodiments of the present invention may also provide, for example, methods for displaying (via a user interface in communication with the dispensing device) prompts for user inputs in a variety of languages as well as methods for displaying elapsed time information related to the dispensing of media by the dispensing device in relation to a medical procedure.

BACKGROUND OF THE INVENTION

Medical procedures, such as imaging procedures, often rely on the use of a media, such as contrast media, flushing media, or other liquid, solid, and/or gas media, that is dispensed and/or injected into the biological structure to be imaged such that the procedure provides more detailed information to a radiologist or other medical personnel responsible for analyzing the procedure results (such as medical imagery). Such medical imaging procedures may include, for instance, angiography, computed tomography (CT), ultrasound and/or NMR/MRI. The term "contrast media", as employed herein, refers to essentially any suitable type of media, as used in the medical arts, that is injected into a patient and, in the context of a medical imaging procedure (such as MR, angiography, ultrasound or CT), facilitates in highlighting selected areas of the patient's body while the patient is being scanned. In addition, the term "contrast media", as employed herein, may also refer to other diagnostic or therapeutic agents for injection into patients. The term "flushing media", as employed herein, refers to essentially any suitable type of medium, such as a saline solution, that can be used to flush contrast medium from the tubing of an infusion system and that is well-suited for flowing through the patient's body so as to serve a useful supplementary purpose, such as keeping his/her veins open in preparation for another infusion of contrast media. Contrast media is often injected into a patient's vasculature prior to the medical imaging procedure by a dispensing device, such as a power injector having an electronic controller and/or a user interface in communication therewith.

Some dispensing devices include electronic controllers and/or user interfaces that are capable of communicating with and/or controlling (in some cases remotely) the dispensing device. For example, in some cases, the controller may allow a user to remotely control the dispensing device from a control room using, for instance, a user interface (such as a touch screen or personal computer) that is in communication with the controller and/or the dispensing device.

In addition, in some medical imaging facilities, the dispensing device may be in communication with an extravasation detection accessory (EDA) (such as the E-Z-EM Extravasation Detection Accessory (EDA®)), or other accessory device capable of detecting extravasation events in a patient undergoing a medical imaging procedure. Such accessories may include, but are note limited to, adhesive electronic sensors capable of being adhered to a patient's skin at the contrast media injection site (in procedures using a power injector, for example). The EDA may thus be capable of detecting changes in impedance at the injection site corresponding to an extravasation event (which may include, for instance, cases wherein contrast media is inadvertently released outside the targeted injection area (i.e., outside the vasculature of the patient). EDA devices may include embedded electronic components that may be in communication with the electronic controller of the dispensing device, such that an operator of the dispensing device may choose whether or not to enable the EDA during a given dispensing operation. In addition, the EDA may generate a data set during the course of its operation during a dispensing operation. For instance, an EDA may, in some cases generate a data set that may be stored either in its embedded electronic components, or sent to the electronic controller of the dispensing device for storage along with the dispensing device data. Such EDA data may include, for example, time and date stamps, an indication as to whether or not the EDA was enabled, and indication of whether or not an extravasation event was detected during a given dispensing operation, and an impedance profile (over time) generated by the EDA as it is adhered to an injection site.

Some dispensing devices used in medical imaging practices are syringe-based power injectors (including the E-Z-EM Empower CT® and Empower CTA® power injector systems) that may include a plurality of syringes (configured to be capable of containing prescribed volumes of contrast and/or flushing media). In addition, such systems are electronically controlled via electronic controllers that may be programmed to administer a variety of contrast media either arterially or intravenously in conjunction with medical imaging procedures. Such systems may include injector rams that are capable of extending and/or retracting so as to enable the dispensing device to fill and/or dispense from one or more syringes.

Conventional dispensing devices allow a user to control the initialization, filling, and/or retracted of individual syringes using a user interface (such as, for instance, arrow keys corresponding to the direction of retraction and extension of the injector ram). However, conventional dispensing systems (including controllers, dispensing devices, EDA's and other accessories) do not allow for the user to initialize, fill, and/or retract multiple syringes engaged with the dispensing device (such as one syringe used for contrast media and an alternate syringe filled with flushing media) with a single user input (such as the touch of a single button or a single touch screen command using the controller and/or user interface). In addition, conventional dispensing systems do not provide a method for adjusting the properties of a user interface (such as the display of an elapsed time from a given dispensing operation or the language of text displayed by a user interface) in communication with the dispensing device without at least cutting the power to the system and/or completely reconfiguring the dispensing system. Thus, using conventional dispensing devices and/or systems, clinicians must take valuable time to initialize and fill multiple syringes (containing, for instance, contrast media and/or flushing media) for certain medical procedures. In addition, the user interface of conventional dispensing devices must be shut down and/or reconfigured in order to adjust user interface display parameters (such as language preferences). In addition, when using conventional dispensing devices, clinicians must utilize separate timing devices to properly ascertain the elapsed time from a given dispensing operation which may distract the clinician from monitoring the user interface of the dispensing device which may indicate important clinical information such as the occurrence of an extravasation event, a fault in the dispensing operation, and/or the amount of media dispensed during a given dispensing operation.

Thus, there exists a need for a device, method, and/or computer program product for controlling multiple initialization, filling, and retraction functions of a medical device, including, but not limited to, a dispensing device or other medical imaging accessory such that a user may more efficiently and more easily control the dispensing device to perform such functions via a single user input. Also, there exists a need for a system, method and/or computer program product capable of modifying the display parameters of a user interface in communication with one or more dispensing devices (or other medical devices of accessories located in a medical suite) such as the language of the text displayed by the user interface, or the display of an elapsed time graphic by the user interface.

SUMMARY OF THE INVENTION

The above and other needs are met by the present invention which, in one alternative embodiment, provides a dispensing medical device, such as a power injector device configured to be capable of dispensing a medium as part of a medical procedure. According to one embodiment, the medical device comprises at least one injector ram adapted to be capable of operably engaging a syringe operably engaged with the medical device, wherein the syringe is adapted to be capable of containing the medium. The injector ram is configured to be capable of performing at least one dispensing function such as, for instance, initializing the syringe prior to filling the syringe with media, filling the syringe with media and/or dispensing media from the syringe. The medical device also includes a controller device capable of actuating (including extending and/or retracting) the injector ram relative to the syringe, and a user interface in communication with the controller device and capable of receiving a user input from a user of the medical device. In addition, the medical device also includes a storage device (such as a memory device) in communication with the controller device and configured to be capable of receiving the user input from the user interface and selectively storing the user input such that the at least one dispensing function may be performed in response to the user input.

In other alternative embodiments, the user interface of the medical device also includes a display and the controller device is configured to be capable of displaying a graphic on the display. In other embodiments, the storage device includes a non-volatile storage medium or other memory device such that the storage device is further configured to be capable of storing a plurality of display formats (such as various written languages to be used to present text data via the display) such that the display may be capable of displaying data in the plurality of different display formats.

According to the method and computer program product embodiments of the present invention, a method for controlling a dispensing device adapted to be capable of dispensing of contrast media as part of a medical imaging procedure is provided. In one alternative embodiment, the method comprises the steps of: receiving a user input from a user interface in communication with the dispensing device; and directing the dispensing device to perform at least one dispensing function in response to the user input such that the dispensing device may independently performing one or more dispensing functions (such as the initialization of one or more syringes) in response to a single user input. The method and computer program products of the invention may further comprise the steps of storing the user input in a memory device in communication with the user interface and updating the user interface in response to the at least one dispensing function.

In another alternative embodiment, the method may further comprise: directing a portion of the data within the usage data set corresponding to an individual medical imaging procedure into a procedure data subset, arranging the procedure data subset by a date of the medical imaging procedure, and displaying data within the usage data set to a user via a user interface.

BRIEF DESCRIPTION OF THE DRAWINGS

Figure 1:
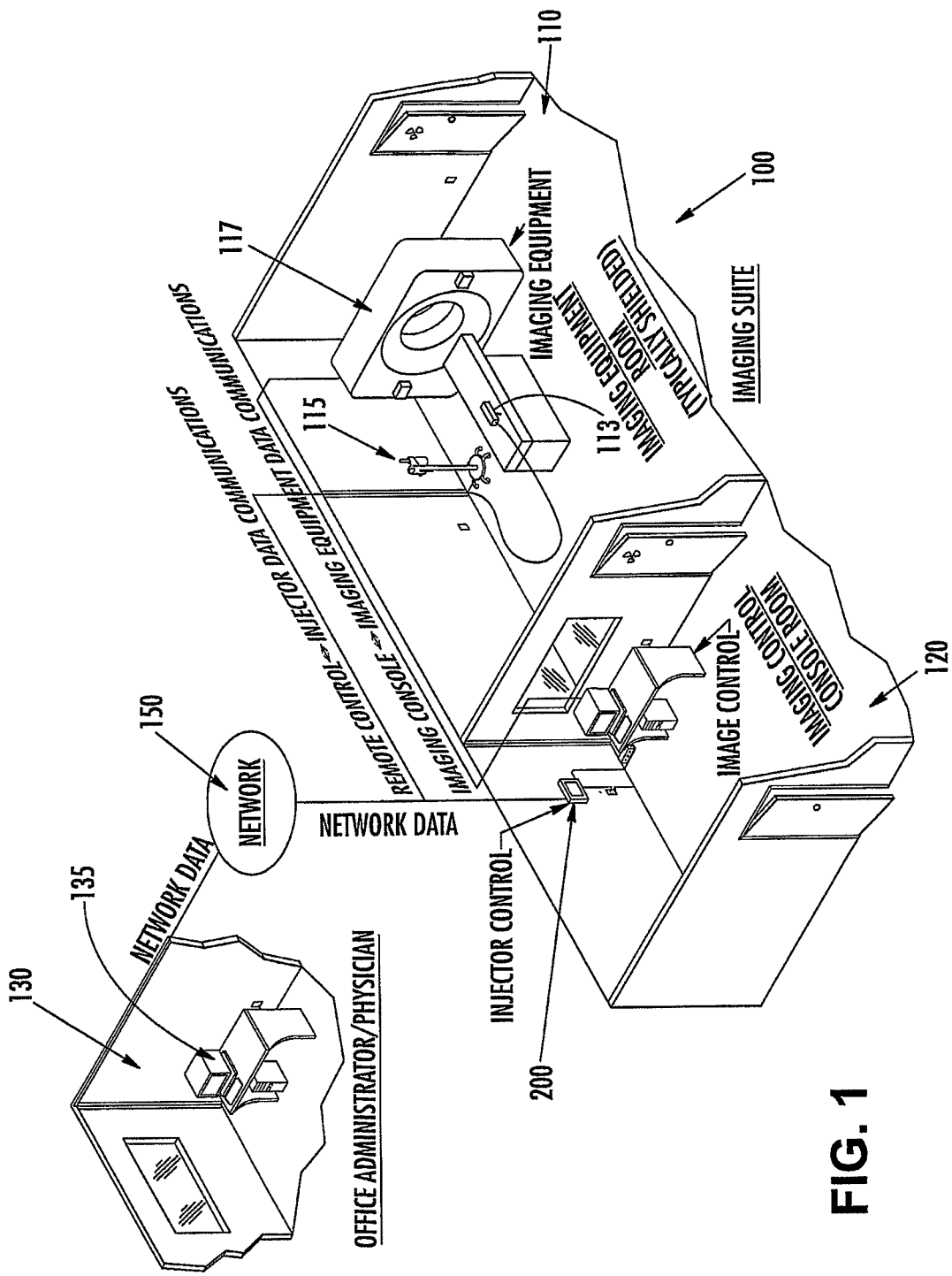
Figure 2:
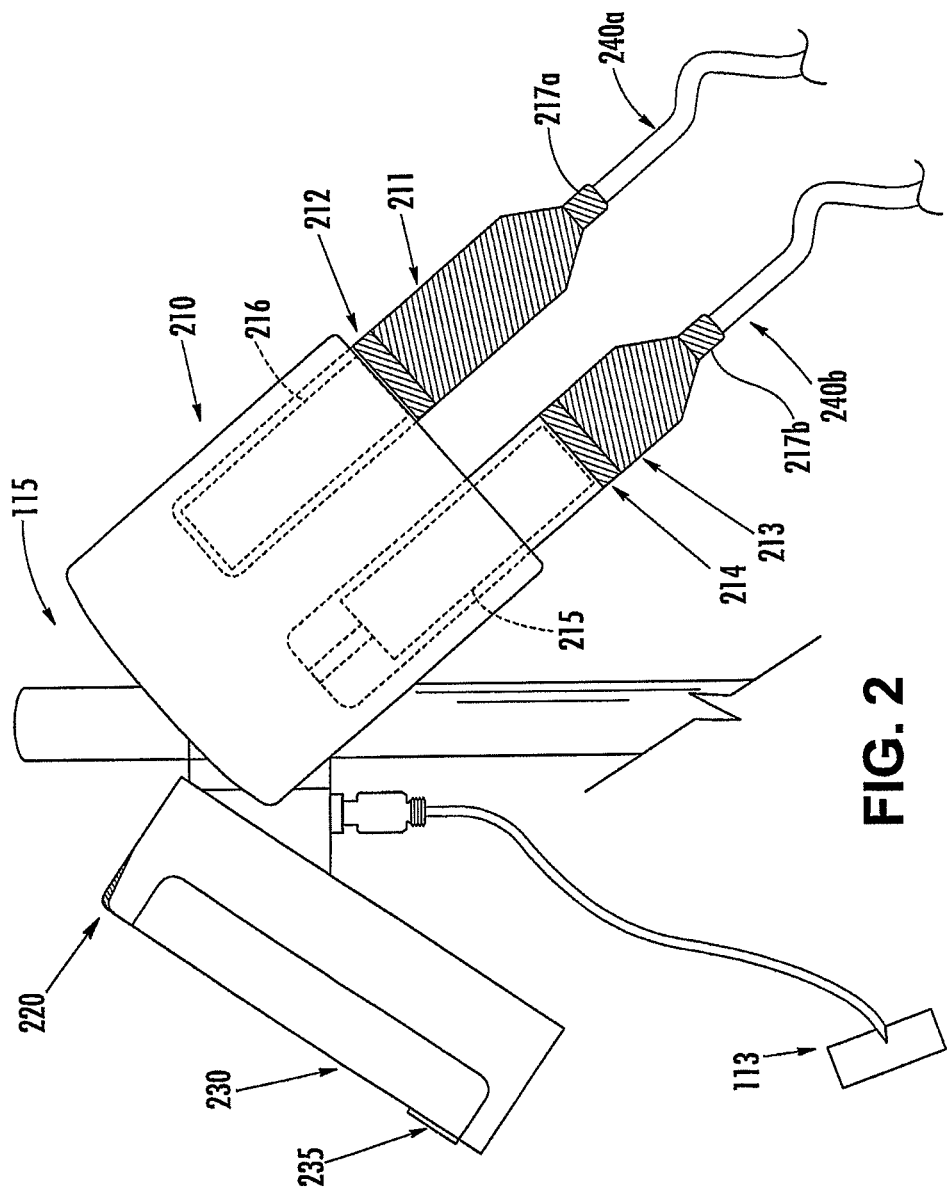
Figure 3A:
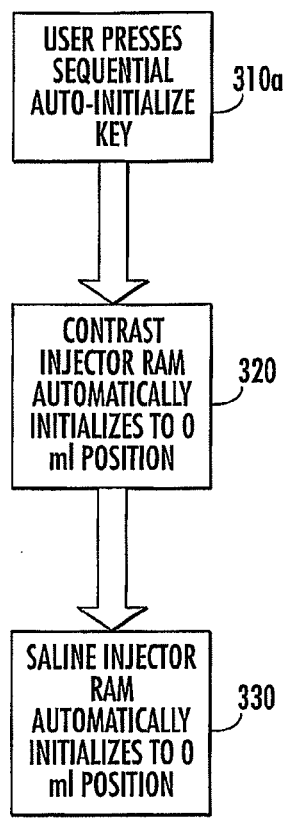
Figure 3B:
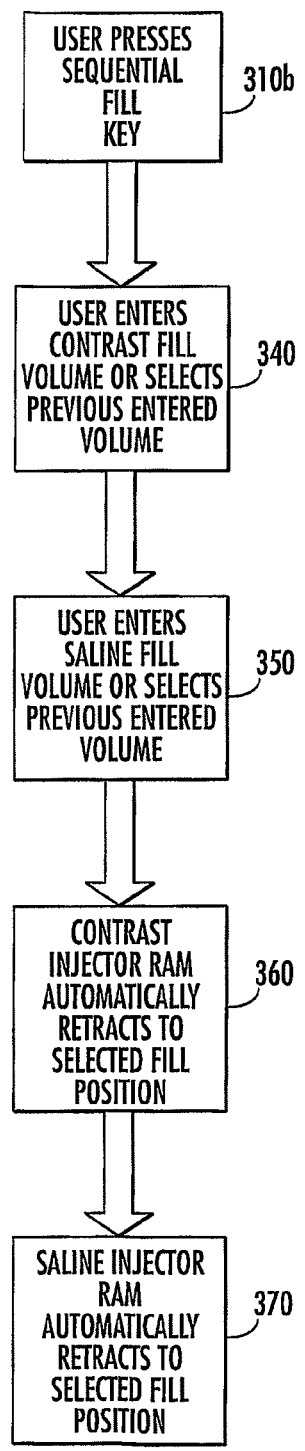
Figure 3C:
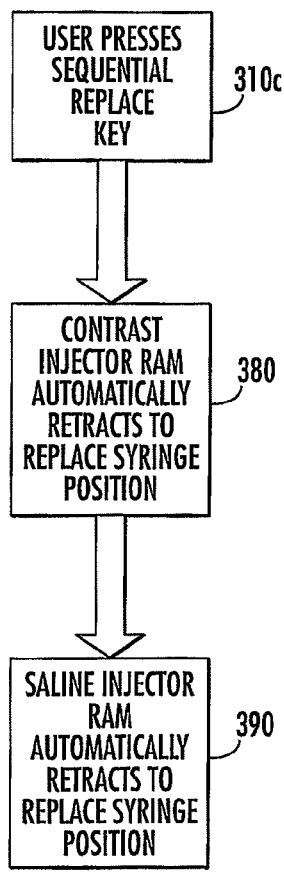
Figure 4:
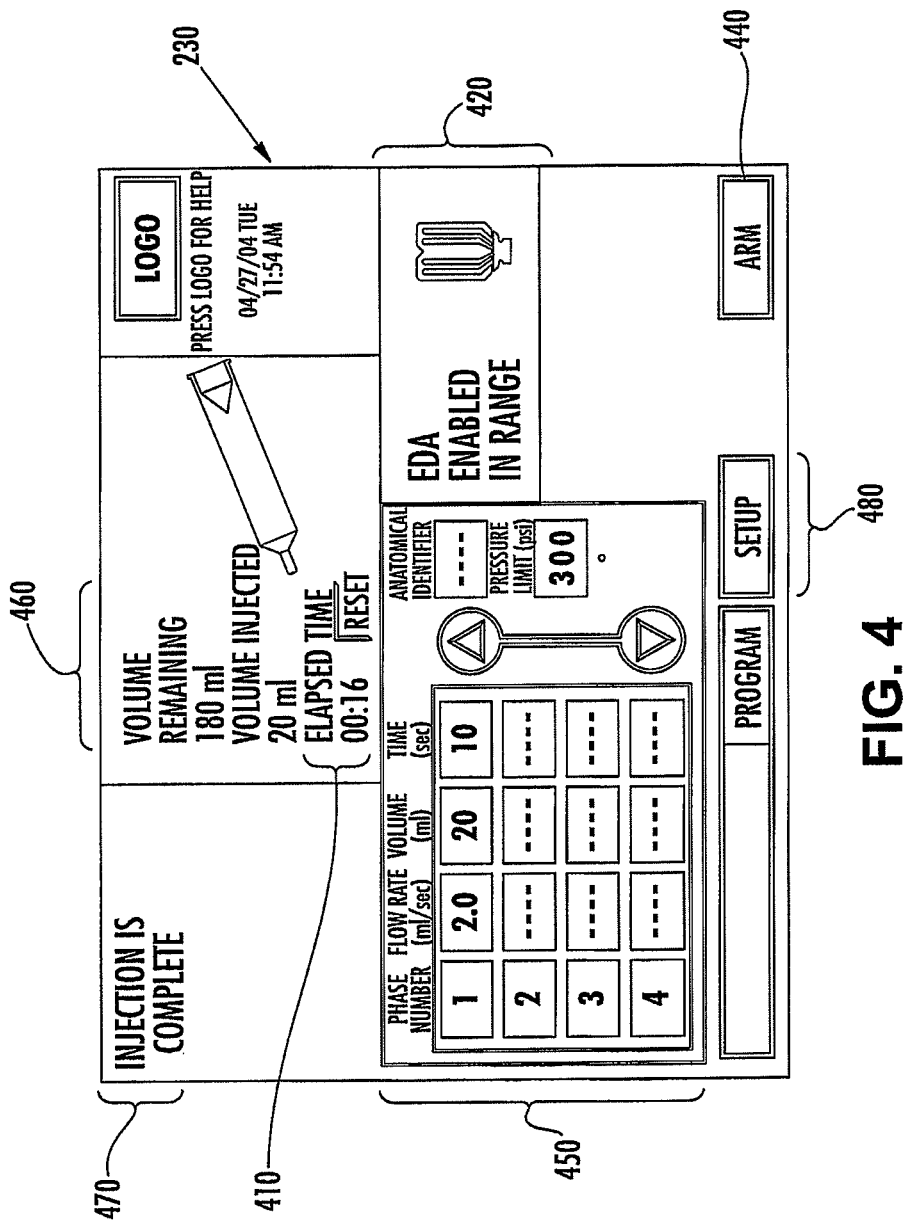

Having thus described the invention in general terms, reference will now be made to the accompanying drawings, which are not necessarily drawn to scale, and wherein:

FIG. 1 shows a non-limiting schematic of a medical imaging suite wherein embodiments of the present invention may be utilized to control a dispensing device capable of performing various dispensing functions (including the initialization, filling, and/or dispensing from one or more syringes) as part of a medical imaging procedure;

FIG. 2 shows a non-limiting schematic of a dispensing device having two injector rams operably engaged with at least two syringes wherein the dispensing device is adapted to be capable of being controlled by the method and/or computer program product of one embodiment of the present invention;

FIG. 3A shows a non-limiting flow chart illustrating the steps of a method for initializing a contrast media syringe and a flushing media syringe via a single user input;

FIG. 3B shows a non-limiting flow chart illustrating the steps of a method for filling a contrast media syringe and a flushing media syringe via a simplified user input;

FIG. 3C shows a non-limiting flow chart illustrating the steps of a method for preparing a contrast media syringe and a flushing media syringe for replacement by fully retracting both injector rams of a dispensing medical device via a single user input;

FIG. 4 shows a non-limiting schematic of information that may be displayed on a user interface according to one alternative embodiment of the computer program product of the present invention.

DETAILED DESCRIPTION OF THE INVENTION

The present inventions will be further described hereinafter with reference to the accompanying drawings, in which some, but not all embodiments of the invention are shown. Indeed, these inventions may be embodied in many different forms and should not be construed as limited to the embodiments set forth herein. In the figures, like numbers refer to like elements throughout.

While the embodiments of the device, system, method, and computer program product for collecting data related to the dispensing of contrast media are described below in the context of collecting data from dispensing medical devices and/or EDA devices in a medical imaging suite using powered injectors, it should be understood that the embodiments of the present invention may also be utilized to collect electronic data and/or data log information from a variety of electronic medical devices that may be utilized in a medical procedure or other medical environment. The device, system, method and computer program product embodiments of the present invention may be used for instance, to collect electronic data from a variety of different types of electronic medical devices, such as various dispensing medical devices or electronic monitoring devices so as to enable a clinical practice manager or other user to more effectively assess usage and/or efficiency of the particular device and/or consumable accessories or materials used in conjunction with the device.

FIG. 1 shows a non-limiting alternative embodiment of the present invention. Here, a medical imaging device 117 is located within a medical suite 100 (such as a medical imaging suite 100) of a hospital, health care facility, and/or any other facility. The medical imaging device 117 may include, but is not limited to, a computed tomography (CT) scanner, a fluoroscope, a positron emission tomography (PET) scanner, a magnetic resonance (MR) scanner, an ultrasound device and/or other imaging device that may require the dispensing of a contrast media to a patient prior to performing the medical imaging procedure so as to enhance the quality of an image produced by the imaging device 117. As used herein, the term "medical suite" 100 refers generally to a room or collection of rooms within, for instance, a hospital or other health care facility, wherein various components of a medical device (such as a medical imaging system 117, dispensing medical device 115, EDA 113, or other components) may be located. The term "medical suite" 100 includes, but is not limited to a medical imaging suite having various components of a medical imaging system located therein. The medical suite 100 may further comprise, for example, a control room 120 where an operator of the medical system may be stationed, as well as a procedure room 110 (such as an imaging room 110) wherein the medical device 117 and other equipment related to a medical imaging procedure may be located (including a dispensing medical device 115, configured to be capable of dispensing a contrast media). The dispensing medical device 115 may comprise various automated dispensing medical devices suitable for dispensing and/or injecting contrast media prior to a medical imaging procedure. For example, the dispensing medical device 115 may comprise a power injector device including one or more syringe dispensing systems configured to be capable of injecting a patient with contrast media and/or flushing media (such as saline solution) prior to a medical imaging procedure. One skilled in the art will appreciate that some electronic dispensing medical devices 115 are capable of performing a dispensing operation (such as initializing, filling, and/or dispensing from a single syringe) in response to a user input (such as the depression of a button). However, in conventional dispensing medical devices 115, the user of the dispensing medical device 115 must initiate each dispensing function (corresponding to each individual syringe) independently with separate user inputs (such as by pressing a sequence of buttons or via a multiple step input process). Therefore, when controlling dispensing medical devices having more than one syringe operably engaged therewith (such as the dispensing medical device 115 shown generally in FIG. 2 and claimed in the present invention) the user is required to monitor and determine the proper user inputs to properly initialize, fill, and/or dispense from multiple syringes (that may contain contrast media, flushing media, and/or combinations thereof). Thus, in one alternative embodiment, the dispensing medical device 115, method and computer program products of the present invention the dispensing functions of a dispensing medical device having one or more syringes operably engaged therewith may be controlled via a simplified user input (such as a single user input that may initiate and direct the controller 220 of the dispensing medical device 115 to complete one or more dispensing functions). In addition, non-limiting examples of the present invention presented herein include devices, methods, and computer program products for adjusting the format, language, and/or display parameters of a display 230 or other user interface 220 of the dispensing medical device 115 such that a user of the device may control the dispensing medical device 115 in a safer and more efficient manner.

FIGS. 1 and 2 show a dispensing medical device 115 configured to be capable of dispensing a contrast and/or flushing media according to one alternative embodiment of the present invention including an injector portion 210 (capable of operably engaging at least two syringes 211, 213) and a controller device 220 configured to be capable of controlling the dispensing operations of the dispensing medical device 115. According to the exemplary embodiment shown in FIG. 2, the dispensing medical device 115 includes a pair of injector rams 215, 216 adapted to be capable of operably engaging a corresponding pair of syringes 211, 213 that are operably engaged with the dispensing medical device 115. The syringes 211, 213 may be attached to the injector portion 210 of the dispensing medical device 115 in a fluid-tight manner. As described above, the syringes 211, 213 may be configured to be capable of containing a fluid media (such as a contrast media and/or flushing media that may be used to enhance the imaging characteristics of an imaging device 117 during a medical imaging procedure). As shown generally in FIG. 2, the syringes may further comprise luer locks 217a, 217b or other fluid-tight connections so as to allow fluid communication between the syringes 211, 213 and polymer tubing 240a, 240b configured to be capable of conveying the media contained within the syringes 211, 213 to an injection site (such as an intravenous line) by extending the injector rams 215, 216 into the syringes 211, 213. In addition, the polymer tubing 240a, 240b may be used to allow fluid communication between the syringes 211, 213 and a container filled with contrast media and/or flushing media such that the syringes 211, 213 may be filled with such media by retracting the plungers 212, 214 into the syringes 211, 213 that may be operably engaged with the dispensing medical device 115. Furthermore, the injector rams 215, 216 may be configured to be capable of performing at least one dispensing function (such as extending and/or retracting) so as to be capable of correspondingly advancing and/or retracting the plungers 212, 214 disposed concentrically within the chambers of the syringes 211, 213 to either dispense from or fill the syringes 211, 213 with fluid media. For example, according to various embodiments of the present invention, the injector rams 215, 216 may be capable of performing dispensing functions including, but not limited to: extending fully into a syringe 211, 213 so as to initialize the syringe 211, 213 prior to filling the syringe with media; extending into the syringe 211, 213 so as to dispense media from the syringe; and retracting from the syringe 211, 213 so as to fill the syringe with the media contained in a storage container.

The dispensing medical device 115 may also comprise a controller device 220 configured to be capable of actuating the injector rams 215, 216 relative to the syringes that may be operably engaged with the dispensing medical device 115. The controller device may comprise, for instance, one or more linear actuators configured to be capable of extending and/or retracting the injector rams 215, 216 at a selected velocity such that the syringes 211, 213 may dispense and/or be filled with media at a selected flow rate. The controller device 220 may further comprise other types of actuator devices suitable for actuating the injector rams and communicating with a computer device or other user interface 230 as described below. The controller device 220 may comprise a microprocessor chip or other computer device suitable for controlling the actuation of the injector rams 215, 216, controlling the communication of data between the various components of the dispensing medical device 115 and other electronic devices in communication via a wired or wireless network 150 and/or facilitating the reception of user inputs from a user interface 230 that may be operably engaged with and/or in communication with the controller device 220 of the dispensing medical device 115. In some instances, the controller device 220 may be located remotely from the injector portion of the dispensing medical device 115 (such as in a control room 120, or in an administrative office 130 that is outside of the medical imaging suite 100). In alternate embodiments, as shown generally in FIG. 1, the controller device 220 of the dispensing medical device 115 may be controlled remotely by a remote control device 200 adapted to be capable of communicating with the dispensing medical device 115 and/or the controller device 220 in communication with the dispensing medical device 115. The terms "remote," "remotely controlled," and located "remotely" as defined herein, may refer to components that are not in physical contact with one another, not operably engaged with one another, and/or not co-located in the same room but that may nonetheless be in communication electronically, mechanically, and/or electromechanically via a number of different communication techniques including, but not limited to, a computer network 150 that may link the various control components (i.e. controller devices 220, personal computers 135, user interfaces 230 (see FIG. 2), and/or remote control devices 200) with the injector portion 210, imaging device 117, or other medical devices that may be located either within or outside the medical imaging suite 100.

The controller device 220 may further comprise a user interface 230 in communication with the controller device 220 and configured to be capable of receiving a user input (such as a keystroke, actuation of a button, or other user input) from a user of the dispensing medical device 115. The user interface may comprise, for example, a touch screen display, LCD, CRT display, or other display types as well as a number of input and/or control devices such as computer devices, keyboards, actuator buttons 235, electronic stylus devices, trackballs, computer mice, joysticks, and/or other devices suitable inputting electronic data to the controller device 220.

Thus, in one alternative embodiment of the present invention, a user may either view, scroll through, annotate, create, and/or modify data corresponding to a dispensing operation of the dispensing medical device 115 on a touch screen that is in communication with and/or integrated with the dispensing medical device 115 or, alternatively, the user may access the data from the controller device 220 via wire or wireless connections (i.e., via the computer network 150) such that the data may appear on a display or personal computer remotely located from the imaging suite 100. In another alternate embodiment of the present invention, a clinical practice manager may be capable of accessing, viewing, and/or manipulating the data corresponding to the dispensing functions of the dispensing medical device 115 via the computer network 150 such that the data may be visible at a personal computer 135 located in an administration office 130 located outside the medical suite 100 (as shown generally in FIG. 1).

In embodiments wherein the user interface 230 comprises a display device, the display may be further configured to be capable of displaying data from a data set corresponding to the at least one dispensing function (such as the extension of the injector rams 215, 216 into the syringes 211, 213 corresponding to the injection of contrast media) such that a user of the dispensing medical device 115 may view data corresponding to the dispensing operation (such as flow rate, elapsed time from injection of media, detection of an extravasation event by an accessory EDA 113, or other data). An example of such a data set is shown generally in FIG. 4 and discussed further below with regard to the method and computer program embodiments of the present invention.

The dispensing medical device 115 may further comprise a storage device (such as a memory module and/or non-volatile data storage medium) integrated with the controller device 220 and/or the injector portion 210 of the dispensing medical device. The storage device may be configured to be in communication with the controller device 220 and be further configured to be capable of receiving the user input from the user interface 230/235 and selectively storing the user input such that the dispensing functions of the dispensing medical device 115 may be performed in response to the user input (such as a single depression of an actuator button 235). For example, according to one exemplary embodiment, the user of the dispensing medical device 115 may press an actuator button 235 and/or input a volume of media to be added to a syringe 211, 213 and these user inputs may be saved as a filling sequence that may be saved by the memory device for subsequent retrieval and use. The user of the dispensing medical device 115 may then activate the filling sequence via a single user input (such as a single depression of an actuator button 235) such that the filling sequence may be initiated by a single user input. The filling sequence may also be performed on one or more syringes 211, 213 and may also include an initiation step wherein the syringe is initialized (i.e. the plunger 212, 214 is fully extended into the syringe 211, 213 so as to reduce the volume of the syringes to a zero-value prior to filling. Exemplary embodiments of such sequences are described below with regard to FIG. 3 and the computer program product embodiments of the present invention.

According to some embodiments of the device of the present invention, the storage device may be configured to be capable of storing a plurality of display formats (including various text languages, font types and sizes, numerical formats, colors, and/or the display of various dispensing tools (including an elapsed time display shown time elapsed from a given dispensing operation)). In such embodiments, the user interface 230 (comprising, for instance, a display) may be further configured to be capable of displaying data in the plurality of display formats discussed generally above. In addition, in some embodiments, the storage device may be further configured to be capable of storing a plurality of different language options such that the user interface 230 (comprising for instance, a display) may be capable of displaying text related to the dispensing operation in a variety of different language formats such that the user interface 230 may be configured for user by users having fluency in different languages. Thus, according to these embodiments, the user interface 230 may be configured after the dispensing medical device 115 is delivered to the site to the predominant language of the site. Furthermore, if the dispensing medical device is relocated or used by a clinician who speaks an alternate language, the memory device (having the capability of storing various text and language formats) allows the user interface 230 to display text in the selected language without the need to shut down and/or reconfigure the dispensing medical device 115.

Furthermore, in another alternative embodiment of the present invention, the controller device 220 of the dispensing medical device 115 may be further adapted to be capable of communicating with an extravasation detection device (EDA) 113 that may be located within the procedure room 110 (such as an imaging room 110) (see generally, FIG. 1) so to be capable of being operably engaged with a patient receiving an injection of media from the dispensing medical device 115. The EDA 113 may also be in communication with the dispensing medical device 115, data collection device 200, and/or other computer devices via a wired and/or wireless computer network 150 (shown generally in FIG. 1 and described in further detail below). Furthermore, the controller device 210 may also be configured to be capable of transmitting and/or receiving an extravasation data set from the EDA 113 such that the storage device of the dispensing medical device 115 may be further configured to be capable of receiving the data within the extravasation data set for a given dispensing operation. In addition, as shown in FIG. 2 the EDA 113 may be in communication with the controller device 220 of the dispensing medical device 115 such that the extravasation data set may be presented and/or displayed via the user interface 230 of the dispensing medical device 115 as shown generally in FIG. 4 (see generally, element 420, showing an exemplary extravasation data set corresponding to an "enabled" EDA 113 that is in communication with the dispensing medical device 115.) Data within the extravasation data set may include, but is not limited to: an indication of whether or not the EDA 113 is enabled, an indication of whether or not an extravasation event is detected during a particular dispensing operation, time and date stamps corresponding to operation of the EDA, and/or other EDA 113 data.

As shown generally in FIG. 1, the dispensing medical device 115 of the present invention, EDA 113 (see below), supplemental electronic devices (i.e., medical imaging devices 117, medical imaging device controllers 122, vital sign monitoring devices) and/or other computer devices may be in communication via a wired and/or wireless computer network 150 that may span over the entire medical imaging suite 100 and beyond (such as to an administrative office 130 and a personal computer 135 located therein).

Furthermore, in another alternative embodiment of the present invention, dispensing medical device 115 may be further adapted to be capable of communicating with an extravasation detection device (EDA) 113 that may be located within the procedure room 110 (such as an imaging room 110) so to be capable of being operably engaged with a patient receiving contrast media from the dispensing medical device 115. The EDA 113 may also be in communication with other computer devices via the wired and/or wireless computer network 150. Furthermore, the controller device 220 of the dispensing medical device 115 may also be configured to be capable of transmitting and receiving an extravasation data set from the EDA 113 such that the storage device of the dispensing medical device 115 may be further configured to be capable of receiving the data within the extravasation data set such that the extravasation data set may be retained within the storage device for a given dispensing operation and/or displayed via the user interface 230 of the dispensing medical device 115.

Furthermore, as shown in FIG. 1, according to some embodiments of the present invention, the controller device 220 of the dispensing medical device 115 may be located in the control room 120 of the medical suite 100 and be in communication with the injector portion 210 of dispensing medical device 115 via a wire connection extending into the imaging room 110 where the injector portion 210 of the dispensing medical device 115 may be located. According to some embodiments, the various electronic devices (including, for instance the dispensing medical device 115, EDA 113, imaging device 117, imaging device controller 122, computer devices 135, and/or electronic vital sign monitoring devices (EKG devices, breath monitoring devices, pulse monitoring devices, blood flowmeters, etc.) may also be in communication via a wired and/or wireless computer network 150, as shown generally in FIG. 1. In other embodiments (as shown generally in FIG. 2) the controller device 220 may be co-located with the injector portion 210 of the dispensing medical device 115. In most embodiments, regardless of the location of the controller device 220 relative to the injector portion 210 of the dispensing medical device 115, the dispensing operations of the dispensing medical device 115 may be controlled by the computer program product embodiments of the present invention (as described below, and as shown generally in FIG. 3) which may run, for instance, on the controller device 220 or on the user interface 230 in communication with the controller device 220. In such embodiments, the computer program product may include executable portions for receiving a user input from a user interface 230 in communication with the dispensing medical device 115, and an executable portion for directing the dispensing medical device 115 to perform at least one dispensing function in response to the user input such that the dispensing medical device 115 is capable of independently performing the at least one dispensing function in response to a single user input (as described in more detail below and shown generally in the schematics flow charts of FIG. 3).

The present invention also provides a method for controlling a dispensing medical device 115 adapted to be capable of dispensing media as part of a medical imaging procedure. According to one exemplary embodiment, the method comprises the steps of receiving a user input from a user interface 230 in communication with the dispensing medical device 115 and directing the dispensing medical device 115 to perform at least one dispensing function (such as the retraction and/or extension of one or more injector rams 215, 216 so as to dispense from and/or fill one or more syringes 211, 213 operably engaged with the dispensing medical device 115) in response to the user input such that the dispensing medical device 115 is capable of independently performing the at least one dispensing function in response to a single user input (such as the touch of an actuating button 235 (see FIG. 2)). The receiving step may comprise, for instance, receiving a user input from a user interface 230 that is co-located with the injector portion 210 of the dispensing medical device 115 as shown generally in FIG. 2. In addition, in some embodiments of the method of the present invention, the receiving step may comprise receiving the user input from a remote control device 200 (see FIG. 1) adapted to be capable of communicating with the dispensing medical device 115 (via, for instance, a computer network 150) from a remote location, such as a control room 120. The user inputs received according to the various method embodiments of the present invention may include, but are not limited to: an initialization command to extend the injector rams 215, 216 into a syringe 211, 213 operably engaged with the dispensing medical device 115; a fill command to retract the injector rams from a syringe operably engaged with the dispensing medical device; a dispense command to extend the injector rams into a syringe operably engaged with the dispensing medical device at a predetermined flow rate; a selection of a language of a text graphic adapted to be displayed by the user interface 230; a selection of the predetermined flow rate corresponding to the dispense command; and a start command to commence a dispensing operation.

FIGS. 3A-3C show schematic flow charts of several embodiments of the method of the present invention wherein the dispensing medical device 115 is directed to perform a plurality of dispensing functions in response to a single user input so as to reduce the work load of a user of the dispensing medical device 115 during the course of a variety of medical imaging procedures or other medical procedures in which the dispensing medical device 115 may be utilized. For instance, as shown in FIG. 3A, step 310a depicts the reception of a user input by the dispensing medical device 115 (in the depicted embodiment, the user input is the depression of a "sequential auto-initialize" key or actuation button 235). The method of FIG. 3A further comprises step 320 wherein the dispensing medical device 115 is directed to automatically extend a first injector ram 215 to an initial position such that a syringe 213 configured to be capable of containing contrast media is initialized to a zero-volume position. In addition, step 330 comprises directing the dispensing medical device 115 to automatically extend a second injector ram to an initial position such that a syringe 211 configured to be capable of containing a flushing media (such as saline solution) is initialized to a zero-volume position. Thus, according to the method embodiment shown in FIG. 3A, the dispensing medical device 115 may be directed to perform to initialization functions in response to a single user input (such as the touch of an actuating button 235 corresponding to an auto-initialize sequence as shown in step 310a of FIG. 3A). In this non-limiting embodiment of the invention, the number of syringes 211, 213 that may be initialized via a single user input may be extended beyond two to, for example, three, four, or more syringes operably engaged with one or more dispensing devices 115 and/or injector portions 210.

FIG. 3B shows an alternate embodiment of the method of the present invention wherein step 310b shows the reception of a user input by the dispensing medical device (such as the depression of a "sequential fill" key or actuation button 235). The method shown in FIG. 3B further comprises the steps 340, 350 of receiving user inputs (via, for instance, the user interface 230) corresponding to a selected fill volume for one or more of the syringes 211, 213 (containing, for instance, contrast media and/or flushing media) that may be operably engaged with the injector portion 210 of the dispensing medical device 115 and/or selecting previously entered fill volumes that may be retained in the memory device that may be in communication with the user interface 230 and/or controller device 220 of the dispensing medical device 115. Finally, steps 360 and 370 of FIG. 3B show the steps of directing the dispensing medical device to retract the injector rams 215, 216 configured to be capable of correspondingly retracting the plungers 212, 214 disposed within the syringes 211, 213 configured to be capable of containing the contrast media and/or flushing media. Furthermore, as steps 360 and 370 are performed, the syringes 211, 213 may be filled with the selected volumes of media in response to the user inputs received as part of steps 310b, 340 and 350. Thus, via the steps of the method embodiment shown in FIG. 3B the dispensing medical device 115 (and the various syringes 211, 213 operably engaged therewith) may be automatically filled to a prescribed volume (that may be entered via user input and/or selected from the memory device in communication with the user interface 230) upon the depression of the "auto-fill" key or other actuation button 335 as shown in step 310a. In this non-limiting embodiment of the invention, the number of syringes 211, 213 and associated media that can be specified for filling via the method schematic shown generally in FIG. 3B could be extended beyond two syringes 211, 213 to three, four, or more syringes that may be operably engaged with one or more dispensing medical devices 115 and/or dispensing portions 210.

FIG. 3C shows the steps of an alternate embodiment of the method of the present invention wherein the injector rams 215, 216 of the injector portion 210 of the dispensing medical device 115 are retracted to a position outside of the syringes 211, 213 such that the syringes may be disengaged from the dispensing medical device 115 for replacement by new syringes. As shown in step 310c, the first method step comprises receiving a user input such that dispensing medical device 115 (or the user interface 230 in communication therewith) may respond to the "sequential replace syringe" input or depression of an actuation button 335. Once receiving the user input, the method further comprises directing the dispensing medical device 115 to perform a dispensing function so as to allow the syringes 211, 213 operably engaged with the injector portion 210 to be replaced. More specifically, the controller device 220 of the dispensing medical device 115 is directed to automatically retract the injector rams 215, 216 (corresponding to both the contrast media syringe 211 and the flushing media syringe 213) such that the injector rams are retracted fully from the syringes (to, for instance, a "replace" position) such that the syringes may be removed from the injector portion 210 of the dispensing medical device 115 by a user of the device as shown in steps 380 and 390. In this non-limiting embodiment of the present invention, the number of syringes 211, 213 that may be retracted to its "replace" position via a single user input could be extended beyond two syringes 211, 213 to three, four, or more syringes that may be operably engaged with one or more dispensing medical devices 115 and/or injector portions 210.

As described generally above and shown generally in FIG. 3B, steps 340, 350, some user inputs (such as contrast media fill volume and/or flushing media fill volume) may be input by a user and stored in the memory device (such as a non-volatile memory module) in communication with the user interface 230 and/or controller device 220 of the dispensing medical device such that the user may automatically select the previously stored user inputs via a single user input (such as the depression of an actuation button 335 corresponding to the "sequential fill" user input (see step 310b of FIG. 3B)). Thus, the user of the dispensing medical device 115 may, according to the various embodiments of the method of the present invention, initiate a complex set of auto-initializing (see FIG. 3A, filling (see FIG. 3B), and/or syringe-replacement (see FIG. 3C) routines by the injector portion 210 of the dispensing device. Thus, the user of the dispensing medical device 115 may more efficiently prepare, use, and/or re-configure the dispensing medical device 115 via the methods of the present invention.

In addition, the method embodiments of the present invention may also comprise the step of updating the user interface 230 in response to the at least one dispensing function. For instance, during the sequential auto-fill method shown in FIG. 3B the user may select a volume of contrast media (see step 340) to be added to the contrast media syringe 211. In response, the controller device 220 of the dispensing medical device 115 may, in turn, direct the user interface 230 to display the volume of contrast media contained within the contrast media syringe 211 during the course of the sequential auto-fill. For instance, the display of the user interface 230 (as shown generally in FIG. 4) may include a graphic 460 and associated text for indicating the volume of contrast media (or in some instances flushing media/saline solution) contained within the syringes 211, 213 operably engaged with the injector portion 210 of the dispensing medical device 115. This updating step may be accomplished, for example, by the controller device 220, which may detect the position of the injector rams 215, 216 relative to the zero-volume position (i.e. fully extended into the syringes 211, 213) so as to be capable of determining the volume of media remaining in any of the syringes 211, 213 operably engaged with the injector portion 210 of the dispensing medical device.

In addition, in some method embodiments of the present invention, the updating step may further comprise displaying data from a data set selected from the group consisting of an elapsed time from a start of the at least one dispensing function (such as the auto-fill function, or the dispensing of a contrast media) (see FIG. 4, timer graphic 410), a dispensing pressure exerted by the dispensing device, an update graphic to convey the status of the dispensing function, and a text graphic to convey text data in a language selected by the user of the dispensing medical device 115.

The present invention may also provide various computer program product embodiments capable of executing the various method steps 310-390 (as shown generally in FIGS. 3A-3C). In one alternative embodiment, the computer program product embodiments of the present invention are capable of controlling a dispensing medical device 115 configured to be capable of dispensing a contrast media as part of a medical imaging procedure and a user interface 230 adapted to be capable of communicating with the dispensing medical device 115 via a computer network 150 or other wire or wireless methods. The computer program product of the present invention may be capable of operating in conjunction with an operating system (including, but not limited to, Windows, Linux, and/or other operating systems known in the art) that may be used as the base operating system for the dispensing medical device 115, controller device 220 of the dispensing medical device 115, user interface 230, personal computers, and/or other electronic devices configured to be capable of communicating via the computer network 150 within the medical suite 100 and beyond. The computer program product of the present invention may comprise an executable portion for receiving a user input from the user interface 230 in communication with the dispensing medical device 115 (as shown generally in steps 310a, 310b, 310c, 340, and 350 of FIGS. 3A-3C) and an executable portion for directing the dispensing medical device 115 to perform at least one dispensing function in response to the user input such that the dispensing medical device 115 is capable of independently performing the at least one dispensing function in response to a single user input (such as the depression of an actuator button 235 that may be included as part of the user interface 230 of the controller device 220 of the dispensing medical device 115 or the input of a media fill volume (as shown generally in steps 340 and 350 of FIG. 3B).

According to some embodiments of the computer program product of the present invention, the executable portion for receiving may further comprise an executable portion (shown generally in FIG. 3A, step 310a) for receiving an initialization command to extend an injector ram 215 into a syringe 211 operably engaged with the dispensing medical device 115. In such embodiments, the initialization command may comprise, for instance, a depression of an actuation button 235 configured as an auto-initialize key. In other embodiments, the executable portion for receiving may comprise receiving a user input such as a fill command to retract an injector ram 215, 216 from a syringe 211, 213 operably engaged with the dispensing medical device 115 so as to initialize the filling of one more syringes 211, 213 with contrast media and/or flushing media as shown generally in FIG. 3B, step 310b. In another alternate embodiment, the executable portion for receiving may also comprise receiving a user input such as a dispense command to extend at least one injector ram 215, 216 into a syringe 211, 213 operably engaged with the dispensing medical device 115 so as to dispense the media at a predetermined flow rate.

According to other embodiments of the computer program product of the present invention, the executable portion for receiving may further comprise receiving other types of user inputs including, but not limited to: a selection of a language (including the selection of a text alphabet corresponding to a selected language) of a text graphic adapted to be displayed by the user interface 230 of the dispensing medical device 115; a selection of the predetermined flow rate corresponding to the dispense command described generally above; and a general start command to commence a dispensing operation. As described generally above with respect to the device embodiments of the present invention, the user inputs may be received via the user interface 230 (which may in turn be in communication with the controller device 220) of the dispensing medical device 115. Thus, the user input may, in some cases, include the depression of a button (such as an actuator button 235 disposed on the user interface 230, the click of a mouse or trackball, the press of a "virtual" button displayed on a touch-screen user interface 230 or via other user interface 230 technologies that will be appreciated by those skilled in the art.

In addition, in some embodiments of the computer program product of the present invention, the computer program product may further comprise an executable portion for storing the user input in a memory device in communication with the user interface 230. Thus, as shown generally in steps 340 and 350 of FIG. 3B, the user of the dispensing medical device may enter and store various user inputs such as a contrast media fill volume (see step 340) or a saline solution fill volume (see step 350) that may be stored by the memory device (such as a non-volatile memory storage device in communication with the controller device 220 and/or user interface 230) and automatically selected by the user in a subsequent dispensing operation. Thus, the computer program product of the present invention may initiate the auto-fill of one or more syringes 211, 213 (see steps 340, 350) via a single user input (such as the depression of a "sequential fill" key, or other actuator button 235 disposed on the user interface 230 of the dispensing medical device 115) by accessing the stored user inputs of contrast media volume and/or flushing media volume that may have been entered and/or stored in steps 340 and 350 of a previous executable portion for receiving as shown generally in FIG. 3B.

According to the various computer program product embodiments of the present invention, the executable portion for receiving may also comprise an executable portion for receiving the user input from a remote control device adapted to be capable of communicating with the dispensing medical device 115. For instance, as shown generally in FIG. 1, in some embodiments, the remote control device may comprise a controller device 200 (such as a remote control) located in a control room 120 that is located remotely from the imaging room 110 where the dispensing medical device 115 (or in some embodiments, the injector portion 210 of the dispensing medical device 115) may be located. Thus, the executable portion for receiving may also enable the user interface 230 to communicate with the controller device 220 and injector portion 210 of the dispensing medical device 115 so as to enable communication and the transfer of user inputs between the various electronic components of the dispensing medical device 115 and other electronic equipment via wired and/or wireless computer network 150.

The executable portion for directing the dispensing medical device 115 to perform at least one dispensing function in response to the user input may, according to some alternative embodiments of the computer program product of the present invention, further comprise various executable portions for actuating the injector rams 215, 216 disposed in the injector portion 210 of the dispensing medical device 115 and/or manipulating the display parameters of the controller device 220 and/or user interface 230 of the dispensing medical device 115 in response to the various user inputs and stored user inputs described generally above with regard to the executable portions for receiving a user input. For instance, in some embodiments as shown generally in FIG. 3B steps 320 and 330, the computer program product may comprise an executable portion for extending at least one injector ram 215, 216 into at least one syringe 211, 213 operably engaged with the dispensing medical device 115 so as to either initialize the syringe 211, 213 to a zero-volume condition, or to dispense contrast media and/or flushing media from the syringe at a predetermined flow rate as part of a dispensing operation. Alternatively, the executable portion for directing may also comprise, for instance, as shown in FIGS. 3B and 3C, steps 360, 370, 380, and 390, an executable portion for retracting at least one injector ram 215, 216 from the at least one syringe 211, 213 operably engaged with the dispensing medical device 115. The executable portion for retracting may thus retract the syringe plunger 212, 214 such that the syringe 211, 213 may be filled to a selected fill volume (with contrast media and/or flushing media) and/or retract the syringe to a fully-retracted position such that the syringe 211, 213 may be disengaged from the injector portion 210 and replaced with one or more new syringes 211, 213.

According to other embodiments of the computer program product of the present invention, the executable portion for directing the dispensing medical device 115 to perform at least one dispensing function in response to the user input may further comprise directing the dispensing medical device 115 (or the controller device 220 in communication therewith) to manipulate and/or adjust the display parameters of the user interface 230 in response to the various user inputs and stored user inputs described generally above with regard to the executable portions for receiving a user input. For example, in some embodiments, the computer program product of the present invention may further comprise an executable portion for displaying a text graphic on the user interface 230, wherein the text graphic is adapted to be capable of conveying a data set to a user of the dispensing medical device 115. For example, as shown generally the schematic of an exemplary user interface 230 display of FIG. 4, the executable portion for displaying may be responsive to a user input (such as the depression of an actuator button 235 or other input received via the user interface 230) to display a volume text graphic 460 conveying the volume of media remaining in a selected syringe 211, 213 as well as a status text graphic 470 indicating the status of a given dispensing operation (such as its completion). Alternative embodiments of the computer program product of the present invention also comprise an executable portion for displaying an elapsed time counter graphic 410, wherein the elapsed time counter graphic is adapted to be capable of updating in real time. In such embodiments, the elapsed time counter graphic 410 may be automatically initiated concurrently with a dispensing function, such as the dispensing of contrast media by the extension of the injector ram 215, 216 into a syringe 211, 213 filled with contrast media. Thus, a user of the dispensing medical device 115 may, using this embodiment of the computer program product of the present invention, monitor the elapsed time since the introduction of contrast media into a patient without the need to activate and/or monitor a timing device that is separate from the user interface 230 of the dispensing medical device 115.

In addition according to some embodiments of the computer program product of the present invention, the user interface 230 may be configured to receive user inputs via, for instance, a setup actuation button 480 which may allow the user of the dispensing medical device 115 to adjust the display parameters of the user interface 230, including, for instance, the language and/or alphabet of the text displayed on the user interface 230 such that users fluent in various languages may choose to have text graphics 460, 470 displayed in a language that they may be better able to read and understand. In addition, as described above with respect to the device embodiments of the present invention, the storage device of the dispensing medical device 115 may be configured to be capable of storing various language and text configurations such that the user (via the controller 220 and user interface 230) may call up and adjust stored display parameters (such as language, alphabet, font, and/or other text and graphic parameters) from the storage device (such as a non-volatile memory module) without the need to shut down and/or completely reconfigure the dispensing medical device 115 between dispensing operations.

While the receiving user inputs executable portions of steps 310a, 310b, and 310c above are shown in terms of a touch-screen user interface 230 as discussed above, the data screens above may also be navigated by other means, including "point-and-click" methods (via a computer mouse, trackpad, and/or other methods that may be appreciate by one skilled in the art). Furthermore, in some embodiments, the user interface 230 may be in communication with a printer, monitor, or other electronic device suitable for displaying and/or printing the displayed information collected, displayed, and/or stored in accordance with the various methods of the present invention.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Throughout the description, where devices, systems, and computer program products are described as having, including, or comprising specific components, or where processes or methods are described as having, including, or comprising specific process or method steps, it is contemplated that devices, systems, and/or computer program products of the present invention may also consist essentially of, or consist of, the recited components, and that the methods of the present invention may also consist essentially of, or consist of the recited method steps. Further, it should be understood that the order of steps or order for performing certain actions are immaterial so long as the invention remains operable. Moreover, two or more steps or actions may be conducted simultaneously.

The content of each of the patent and non-patent documents referred to herein is expressly incorporated herein by reference in its entirety.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

Also, the invention may suitably comprise, consist of, or consist essentially of the elements or method steps described herein. Further, the invention described herein suitably may be practiced in the absence of any element or process step which is or is not disclosed herein.

We claim:

1. A medical device configured to dispense a medium as part of a medical procedure, the device comprising:
    a plurality of injector rams each associated with at least one respective syringe, each syringe operably coupled to the medical device and configured to contain the medium, and each injector ram configured to be extended and/or retracted within a respective syringe;
    a controller device configured to actuate each of the plurality of injector rams to extend and/or retract relative to the at least one respective syringe;
    a user interface in communication with the controller device and configured to receive a user input from a user of the medical device; and
    a storage device configured to be in communication with the controller device, the storage device further configured to receive the user input from the user interface and selectively store the user input such that the plurality of injector rams are configured to be actuated in response to a single user input.

2. A medical device according to claim 1, wherein the user interface further comprises a display and wherein the controller device is further configured to display a graphic on the display.

3. A medical device according to claim 1, wherein in response to a single user input, the plurality of injector rams are configured to be at least one of:
    extended fully into the at least one respective syringe so as to initialize the at least one respective syringe prior to filling the at least one respective syringe with the media;
    extended into the at least one respective syringe so as to dispense the media from the at least one respective syringe;
    retracted from the at least one respective syringe so as to fill the at least one respective syringe with the media; or
    retracted fully from the at least one respective syringe as to allow for replacement of the syringes.

4. A medical device according to claim 1, wherein the plurality of injector rams are configured to be extended and retracted relative to a respective syringe in response to a single user input.

5. A medical device according to claim 1, wherein in response to a single user input, the plurality of injector rams are configured to be at least one of:
    extended fully into the at least one respective syringe so as to initialize the syringes prior to filling the syringes with media; or
    retracted fully from the at least one respective syringe so as to allow for replacement of the respective syringes.

6. A medical device according to claim 1, wherein the user interface is configured to receive a plurality of user inputs and the storage device is configured to store the plurality of user inputs, and wherein the plurality of injector rams are configured to be actuated based on the plurality of stored user inputs in response to the single user input.

7. A method for controlling a dispensing device comprising a plurality of injector rams each associated with at least one respective syringe, the dispensing device adapted to dispense contrast media as part of a medical imaging procedure, the method comprising:
    receiving a single user input from a user interface in communication with the dispensing device; and
    actuating the dispensing device to extend and/or retract the plurality of injector rams relative to at least one respective syringe in response to the single user input.

8. A method according to claim 7, further comprising storing the user input in a memory device in communication with the user interface.

9. A method according to claim 8, wherein the receiving step comprises receiving a plurality of user inputs and storing the plurality of user inputs in the memory device, and wherein the directing step comprises directing the dispensing device to actuate the dispensing device based on the plurality of stored user inputs in response to the single user input.

10. A method according to claim 7, further comprising updating the user interface in response to actuating the dispensing device.

11. A method according to claim 7, wherein the receiving step comprises receiving at least one of:
    an initialization command to extend the plurality of injector rams into the at least one respective syringe operably coupled to the dispensing device;
    a fill command to retract the plurality of injector rams from the at least one respective syringe operably coupled to the dispensing device;
    a dispense command to extend the plurality of injector rams into the at least one respective syringe operably coupled to the dispensing device at a predetermined flow rate; or
    a replace command to retract the plurality of injector rams fully from the at least one respective syringe so as to allow for replacement of the syringes.

12. A method according to claim 7, further comprising receiving a user input comprising at least one of:
    a selection of a language of a text graphic adapted to be displayed by the user interface;
    a selection of the predetermined flow rate corresponding to the dispense command; or
    a start command to commence actuating the dispensing device.

13. A method according to claim 7, wherein the actuating step comprises at least one of:
- extending the plurality of injector rams into the at least one respective syringe operably coupled to the dispensing device so as to initialize the at least one respective syringe prior to filling the at least one respective syringe with the media;
- extending the plurality of injector rams into the at least one respective syringe operably coupled to the dispensing device so as to dispense the media from the at least one respective syringe;
- retracting the plurality of injector ram from the at least one respective syringe operably coupled to the dispensing device so as to fill the at least one respective syringe with contrast media or flushing media; or
- retracting the plurality of injector rams fully from the at least one respective syringe so as to allow for replacement of the syringes.

14. A method according to claim 7, further comprising at least one of:
- displaying a text graphic on the user interface, wherein the text graphic is adapted to convey a data set to a user of the dispensing device; or
- displaying an elapsed time counter graphic, wherein the elapsed time counter graphic is adapted to update in real time.

15. A method according to claim 7, wherein the directing step comprises actuating the dispensing device to extend and retract each injector ram relative to the at least one respective syringe in response to a single user input.

16. A method according to claim 7, wherein the directing step comprises at least one of:
- extending the plurality of injector rams fully into the at least one respective syringe operably engaged with the dispensing device so as to initialize the syringe prior to filling the syringes with media; or
- retracting the plurality of injector rams fully from the at least one respective syringe so as to allow for replacement of the syringes.

17. A computer-readable storage medium comprising computer-readable program code portions stored therein for controlling a dispensing device comprising a plurality of injector rams each associated with at least one respective syringe, the dispensing device adapted to dispense contrast media as part of a medical imaging procedure, the computer-readable program code portions comprising:
- an executable portion for receiving a single user input from a user interface in communication with the dispensing device; and
- an executable portion for actuating the dispensing device to extend and/or retract the plurality of injector rams relative to at least one respective syringe in response to the single user input.

18. A medical device configured to be capable of dispensing a contrast media as part of a medical procedure, the device comprising:
- at least one injector ram adapted to engage at least one syringe, the syringe operably engaged with the medical device and configured to contain a media, the at least one injector ram configured to be extended and/or retracted within the syringe;
- a controller device configured to actuate the at least one injector ram to extend and/or retract relative to the at least one syringe;
- a user interface in communication with the controller device and configured to receive a plurality of user inputs from a user of the medical device;
- a storage device configured to communicate with the controller device, the storage device further configured to receive the user inputs from the user interface and selectively store the user inputs such that the at least one injector ram is configured to be actuated based on the plurality of stored user inputs.

19. A medical device according to claim 18, wherein the at least one injector ram is configured to be actuated in response to a single user input.

20. A medical device according to claim 18, wherein the at least one injector ram is configured to be extended and retracted relative to the at least one syringe based on the plurality of stored user inputs.

21. A method for controlling a dispensing device comprising at least one injector ram adapted to engage at least one syringe, the dispensing device configured to be actuated to extend and/or retract the at least one injector ram within the syringe, the dispensing device adapted to dispense contrast media as part of a medical imaging procedure, the method comprising:
- receiving a plurality of user inputs from a user interface in communication with the dispensing device;
- storing the plurality of user inputs in a memory device in communication with the user interface; and
- directing the dispensing device to actuate the at least one injector ram based on the plurality of stored user inputs.

22. A method according to claim 21, wherein the directing step comprises directing the dispensing device to actuate the at least one injector ram in response to a single user input.

23. A method according to claim 21, wherein the directing step comprises actuating the at least one injector ram to be extended and retracted relative to the at least one respective syringe based on the plurality of stored user inputs.

* * * * *